United States Patent [19]

Pastor et al.

[11] 4,128,589

[45] Dec. 5, 1978

[54] GENERATION OF $CF_4$ FROM TEFLON FOR REACTIVE ATMOSPHERE PROCESSING AND GROWTH OF METAL FLUORIDES

[75] Inventors: Ricardo C. Pastor, Manhattan Beach; Morton Robinson, Malibu, both of Calif.

[73] Assignee: Hughes Aircraft Company, Culver City, Calif.

[21] Appl. No.: 808,844

[22] Filed: Jun. 22, 1977

[51] Int. Cl.$^2$ ............................................. C07C 21/18
[52] U.S. Cl. ................................ 260/653; 23/305 R; 252/301.4 H; 260/653.1 R; 260/653.3; 423/491
[58] Field of Search .............. 260/653, 653.3, 653.1 R

[56] References Cited

U.S. PATENT DOCUMENTS

| | | | |
|---|---|---|---|
| 2,933,536 | 4/1960 | Wall et al. | 260/653.1 R |
| 2,978,519 | 4/1961 | Fischer | 260/653.1 R |
| 3,223,739 | 12/1965 | Teumac | 260/653.1 R |
| 3,832,411 | 8/1974 | Arkles et al. | 260/653.3 |
| 4,076,760 | 2/1978 | Hartwimmer | 260/653 |

*Primary Examiner*—C. Davis
*Attorney, Agent, or Firm*—B. T. Hogan, Jr.; W. H. MacAllister

[57] ABSTRACT

A tetrafluoromethane ($CF_4$) generator and process is disclosed that facilitates the relatively low temperature production of $CF_4$ gas via controlled decomposition of polytetrafluoroethylene (Teflon) and tetrafluoroethylene ($C_2F_4$). $CF_4$ produced via this process proves to be an excellent $OH^-$ scavenger in the processing and growth of metal fluoride single crystals.

6 Claims, 9 Drawing Figures

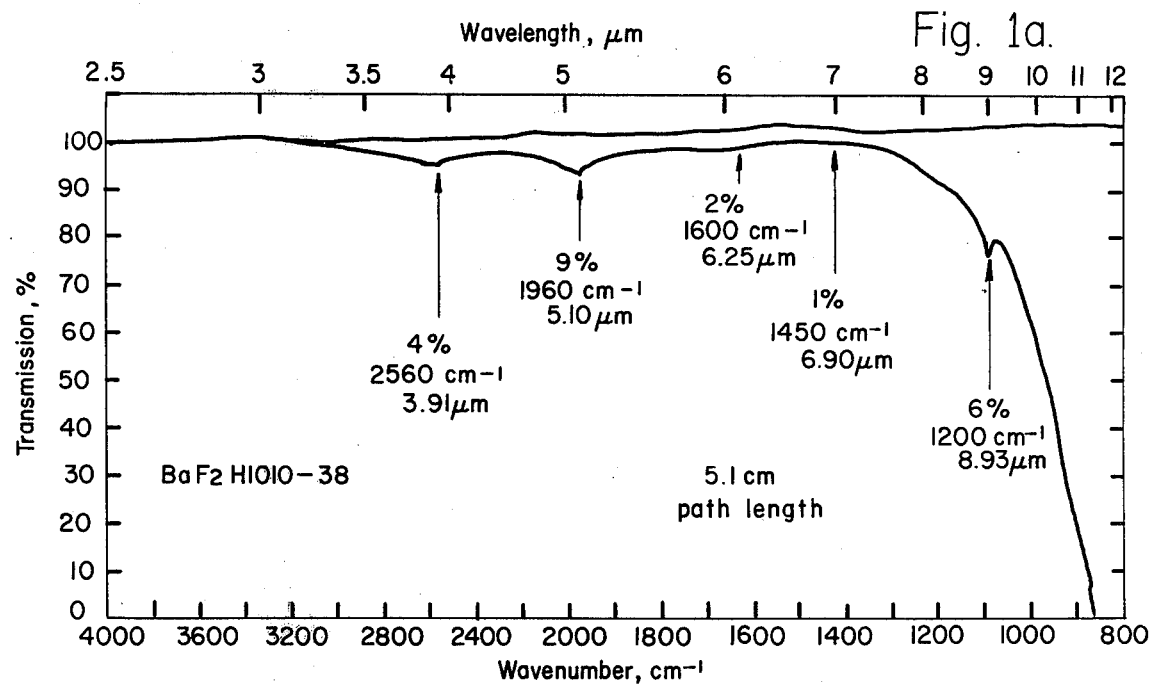
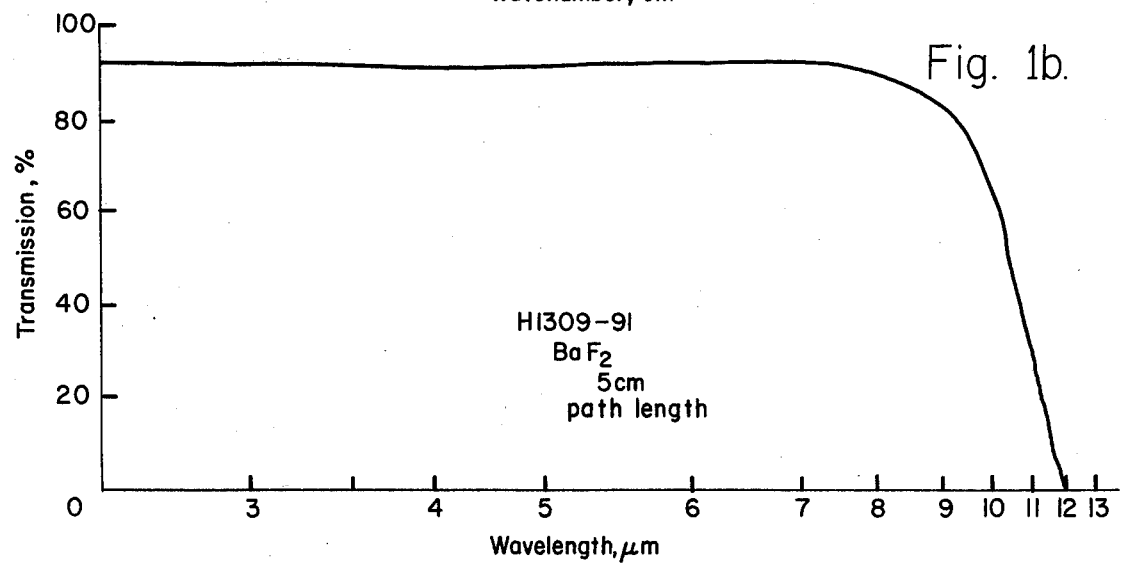
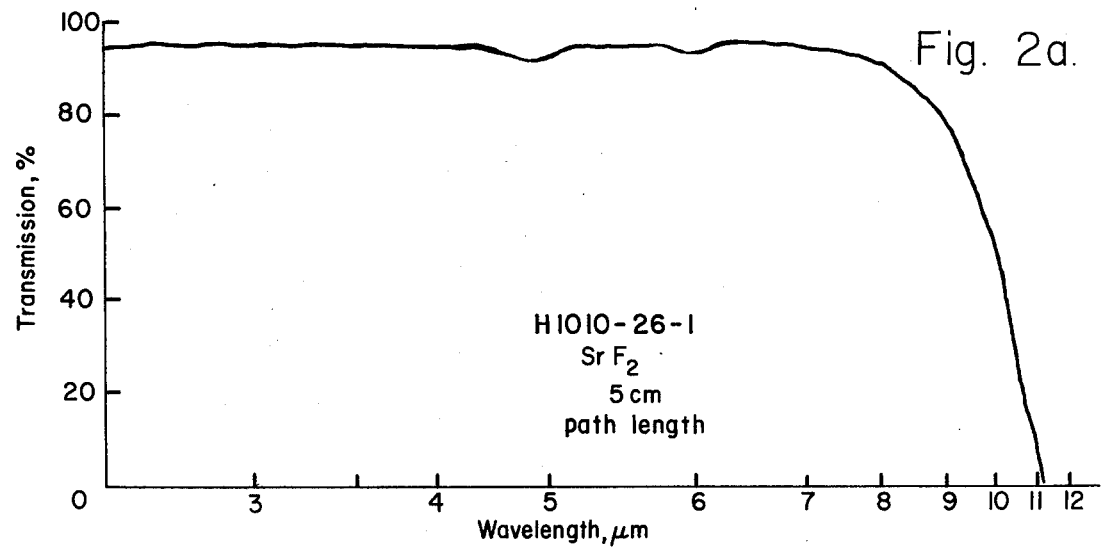

GENERATION OF CF₄ FROM TEFLON FOR REACTIVE ATMOSPHERE PROCESSING AND GROWTH OF METAL FLUORIDES

The Government has rights in this invention pursuant to Contract No. F33615-74-C-5115, awarded by the United States Air Force.

BACKGROUND OF THE INVENTION

1. Field of the Invention

This invention is directed to the formation of $CF_4$ gas in general and to the formation of $CF_4$ gas in a controlled manner from Teflon in particular.

2. Description of Prior Art

The production of large ultra-pure metal fluoride single crystals suitable for use in high power laser applications, was described in U.S. Pat. No. 3,649,552 issued to Applicant Morton Robinson herein and Donald M. Cripe. In the 3,649,552 Patent, HF gas in a He carrier is shown to be an effective scavenger of oxide impurities found during the growth of fluoride single crystals in a modified Stockbarger type furnace. The furnace was operated at temperatures on the order of 1500° C. and HF gas was obtained from a cylinder. This process, which later came to be recognized as a relative atmosphere processing (RAP) process had as its principal objective the suppression of hydrolysis during crystal growth in accordance with the following expression:

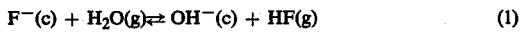

$$F^-(c) + H_2O(g) \rightleftarrows OH^-(c) + HF(g) \quad (1)$$

The forward direction of Eq. (1) shows hydrolysis of the condensed phase (c) by $H_2O$ molecules in the gas phase (g). The reverse direction of Eq. (1) shows the removal of the hydrolysis product, $OH^-$, an undesired anion impurity found in, and on the surface of, metal fluoride crystals.

From the mass-action principle, it follows that in order to effect a very low ratio of $OH^-(c):F^-(c)$, one must provide a low ratio for the pressures of the sources in the gas phase, $P(H_2O)/P(HF)$. This latter ratio, the sole material parameter of the growth process, is called the RAP-index.

The use of HF/He, as taught in the 3,649,552 Patent, leads to a low RAP-index by increasing the denominator of the source pressures discussed above. Thus, the method is limited by the steady state value of the numerator, $P(H_2O)$.

A similar use of HF as a getter or scavenger during a crystal growth process is disclosed in U.S. Pat. No. 3,769,230 issued to Applicant Morton Robinson and Donald P. Devor in October of 1973. Like the 3,649,552 Patent, this patent teaches the use of a HF/He gas purge at some elevated temperature to eliminate anion impurities. It differs significantly from the teachings of the instant invention in that it does not address the production of $CF_4$ gas as a reliable cheap fluoridizing agent, and it does not suggest a way to achieve a lower RAP-index to increase the additional scavenging effect needed to produce ultra-pure metal fluoride crystals.

An HF atmosphere was also disclosed, in U.S. Pat. No. 3,959,442 issued to the Applicants herein on May 25, 1976, to be effective for promoting the congruent melt crystal growth of laser emission compounds.

In order to provide additional scavenging, additional sources of reactive fluorine compounds were sought. Mixtures of HF and $CF_4$ in He proved to be effective but commercially available $CF_4$ is very expensive. Therefore, alternative methods of producing $CF_4$ are needed.

Crystal growers in the USSR have used Teflon (the well-known trademark for polytetrafluoroethylene resins) in their crystal growth apparatus to generate $C_2F_4$. However, they claim that $C_2F_4$ did not decompose into $CF_4$ and C until 1200° C., an undesirable high process temperature for the growth of alkaline-earth flourides which occurs at temperatures above 1200° C. In such cases, workers have observed that carbon becomes intimately mixed with the melt. Consequently, the melt is useless for crystal growth (see E. N. Chernevskaya and Z. N. Korneva, "The Production of Fluorite Crystals in an Atmosphere Containing Fluorine," Sov. J. Opt. Tech. 39, 213(1972)).

Applicants herein know of no additional art related to the decomposition of Teflon to generate $CF_4$ or dissociable fluorine compounds or of art related to the use of fluoridizing agents to achieve a low RAP-index during the growth of metal fluoride crystals.

THE INVENTION

SUMMARY OF THE INVENTION

In seeking to develop a crystal growth process which yields large ultra-pure (with respect to anions) fluoride single crystals by providing a low RAP-index, we established as an objective of this invention the provision of a process for the generation of low cost $CF_4$ gas from Teflon.

A second objective of this invention is to provide $CF_4$ gas at relatively low temperatures.

A still further objective of this invention is to provide $CF_4$ gas at flow rates which facilitate the reliable maintenance of a low RAP-index during the crystal growth process.

In achieving the above-stated objectives while avoiding the disadvantages of the afore-stated prior art, we have discovered a process and developed a novel apparatus comprised of a chamber which facilitates the controlled depolymerization of Teflon into $C_2F_4$ and a pyrolysis chamber for the decomposition of $C_2F_4$ into C + $CF_4$ at relatively low temperatures.

The process for controlling the depolymerization of Teflon and the subsequent dissociation of $C_2F_4$ into C and $CF_4$ which minimizes the production of elemental carbon in the effluent $CF_4$ gas and its subsequent introduction into the melt takes place at relatively low temperatures in a sequential manner which unlike prior art processes is highly predictable and controllable.

The apparatus is of a two-stage design which facilitates the decomposition of Teflon at a relatively low temperature thereby generating $C_2F_4$ at a rate slow enough to allow it to dissociate into $CF_4$ and C prior to exiting the chamber.

The process parameters are temperature and carrier gas flow rates which must be controlled with particularity.

BRIEF DESCRIPTION OF THE DRAWINGS

FIG. 1 consists of graphs which show the effect of using (HF-$CF_4$)/He mixtures during crystal preparation on the infrared spectra of $BaF_2$ crystals. The IR spectrum of a $BaF_2$ crystal grown without the use of $CF_4$ is shown in FIG. 1a. FIG. 1b shows the spectrum of a $BaF_2$ crystal grown with $CF_4$.

FIG. 2 consists of graphs which show the effect of using (HF-$CF_4$)/He mixtures during crystal growth on the infrared spectra of SrF$_2$ crystals. FIG. 2a shows the IR spectrum of a SrF$_2$ crystal grown without CF$_4$ while

FIG. 3 consists of graphs which show the effect of using (HF-CF$_4$)/He mixtures during crystal growth on the infrared spectra of Sr$_{0.34}$ Ba$_{0.66}$ F$_2$ single crystals.

DETAILED DESCRIPTION OF THE INVENTION

This invention is a process and apparatus designed to facilitate the production of CF$_4$ from Teflon to be used in the Reactive Atmosphere Processing (RAP) of alkaline earth and other metal fluoride single crystals.

Our studies have produced evidence which indicates that P(H$_2$O) (the limiting factor in the avoidance of hydrolysis during crystal formation) is determined by the outgas in the growth apparatus. With the dewpoint of the entering gas mixture of HF/He equivalent to a few parts per million H$_2$O content, the OH$^-$(c):F$^-$(c) measured in an HoF$_3$ single crystal suggests an H$_2$O content in the growth region that is larger than desired by three orders of magnitude. Therefore, in order to lower the RAP-index further, scavenging of H$_2$O(g) is needed in addition to that provided by the use of HF/He.

From our experience with RAP using tetrahalomethane, we expected to achieve scavenging of H$_2$O by CF$_4$ in accordance with the following reaction:

$$CF_4(g) + 2H_2O(g) \rightleftharpoons 4HF(g) + CO_2(g) \qquad (2)$$

The forward direction of Eq. (2) is favored thermodynamically, as seen in the equilibrium constants 6.8 × 10$^{27}$ atm$^2$ at 1200° K. and 1.9 × 10$^{25}$ atm$^2$ at 1500° K.

Further evidence that the reaction rates of CF$_4$ would be realistic for the purpose of crystal growth is shown in the following table:

Table I.

| $\frac{[H_2O]}{[CF_4]} 10^{2a}$ | Reaction of CF$_4$ with H$_2$O in Graphite | | | |
|---|---|---|---|---|
| | $\frac{[HF]}{4[CF_4]} 10^2$ | | $\frac{[HF]}{2[H_2O]} 10^2$ | |
| | 900° C | 1000° C | 900° C | 1000° C |
| (0.0) | 0.13 | — | (100) | (100) |
| 2.6 | 0.06 | 0.13 | 4.3 | 9.6 |
| 12.0 | 0.05 | 0.17 | 0.85 | 2.8 |
| 55.0 | 0.05 | 0.16 | 0.19 | 0.59 |

$^a$ The value of (0.0) refers to H$_2$O from outgassing of the apparatus, 12 to saturation of the gas at 0° C and 55 to saturation at 25° C. The gas was 5 mol% CF$_4$ in He. The value of 2.6 was obtained by saturation of pure CF$_4$ with H$_2$O at 25° C.

The values shown in the table were obtained at an effluent flow of 0.4 cm$^3$/sec. through a graphite pyrolysis chamber with an outgas surface area of 190 cm$^2$ and a residence time of 500 sec. It can be concluded from these measurements that for 100% conversion of H$_2$O to HF, the concentration ratio of [H$_2$O]:[CF$_4$] is 1:10$^3$ at 900° C. and 1:10 at $\geq$ 1300° C.

Figure 2B:
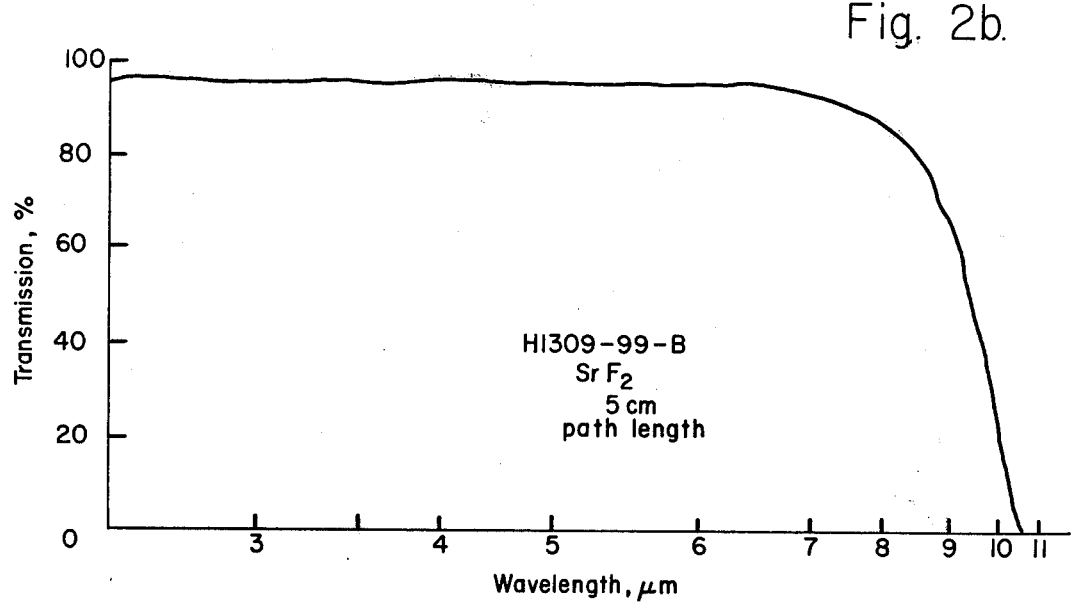
FIG. 2b shows an IR spectrum of SrF$_2$ grown in the presence of CF$_4$.
Figure 3A:
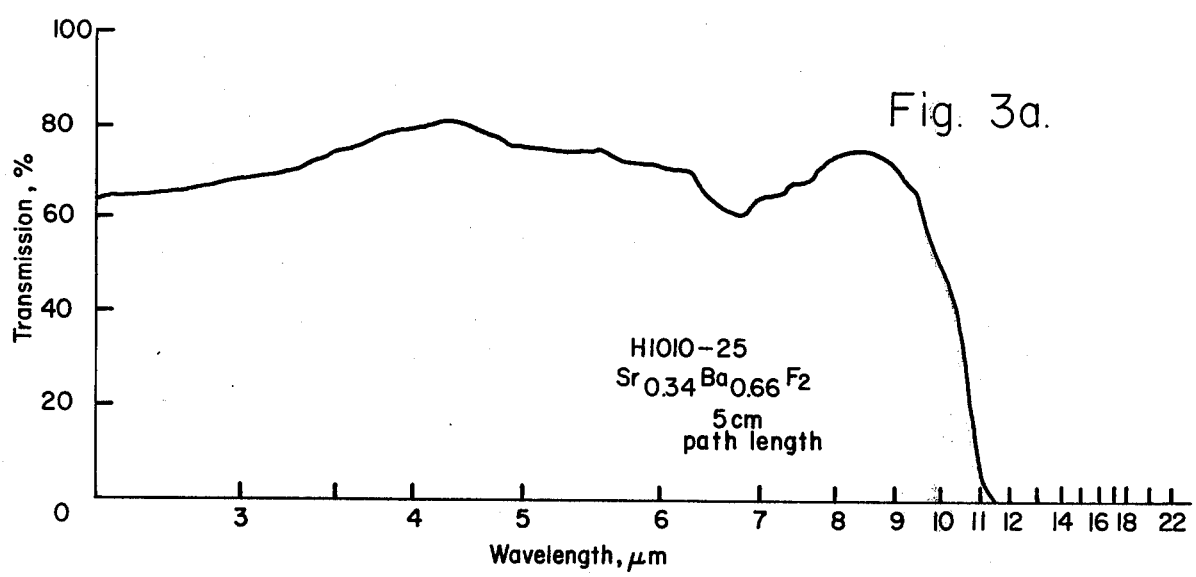
FIG. 3a shows the IR spectrum of an untreated crystal and FIG. 3b shows the IR spectrum of a crystal grown in the presence of CF$_4$.
Figure 3B:
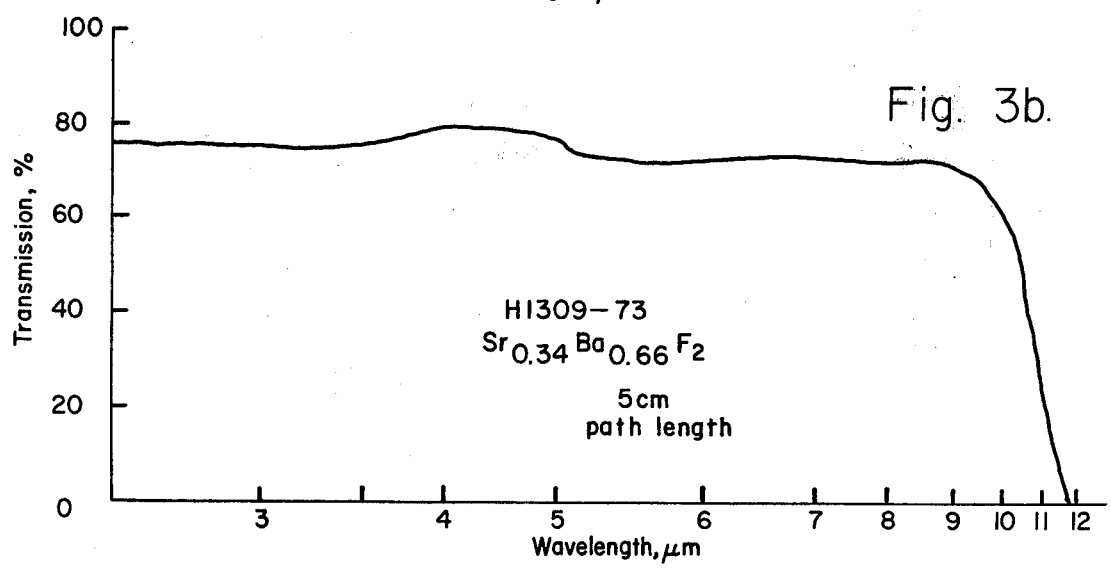

These computations and the results of infrared transmission measurements on single crystals prepared with mixtures of (HF-CF$_4$)/He as the scavenging gas shown in FIGS. 1, 2, and 3 verify that there is an improvement in the transparency of single-crystal alkaline earth fluorides and their solid solutions from the use of HF/He to (HF-CF$_4$)/He. However, the large volume of CF$_4$ needed imposes a severe limitation on the use of this material when viewed in the light of the cost of commercially available CF$_4$ (Freon 14).

It is because of the expense associated with the use of CF$_4$ and the comparative low cost of Teflon that studies were undertaken to ascertain if Teflon could be used as a reliable source of CF$_4$. Our invention therefore involves the controlled depolymerization of Teflon to yield C$_2$F$_4$ vapor, $$(C_2F_4)_n \rightarrow nC_2F_4 \qquad (3)$$

and the quantitative decomposition of C$_2$F$_4$ to CF$_4$, $$C_2F_4 \rightarrow C + CF_4 \qquad (4)$$

Figure 4:
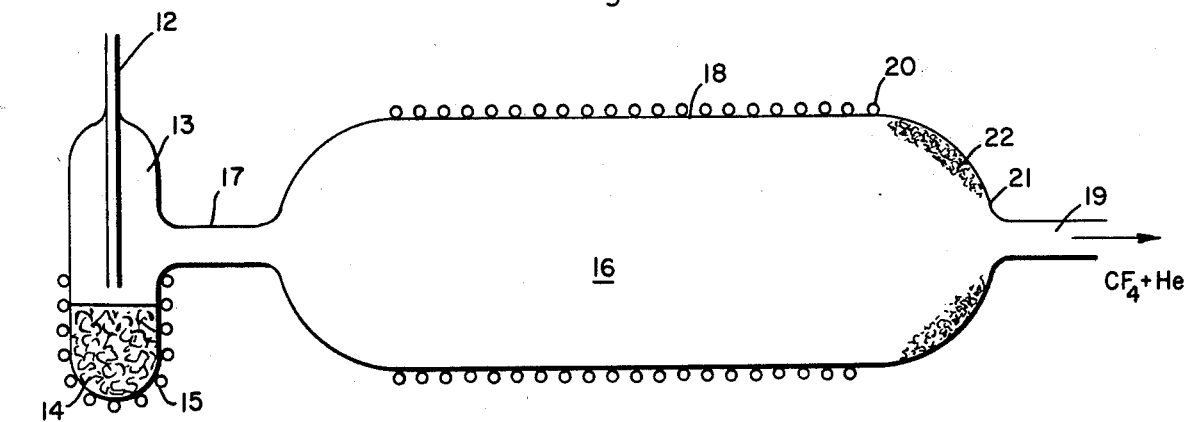
FIG. 4 is a schematic of the invention apparatus.

In order to achieve the results of Eqs. 3 and 4, we designed a reaction chamber or generator from vitreous silica which allows one to control the temperature and pressure of the reaction very closely. Referring to FIG. 4, the scope of this apparatus may be understood to be fabricated from vitreous silica or another similar high density, low porosity material exhibiting high thermal and oxidative resistance. (We are currently using an apparatus fabricated from nickel.) It is provided with a gas inlet means 12 which extends into the first stage ampoule 13 which serves as the primary receptacle for the Teflon 14 to be depolymerized.

The exterior of the first stage ampoule 13 is surrounded by a first furnace 15 used to raise the temperature of the ampoule 13 and the Teflon 14 to the depolymerization temperature of Teflon.

Figure 5:
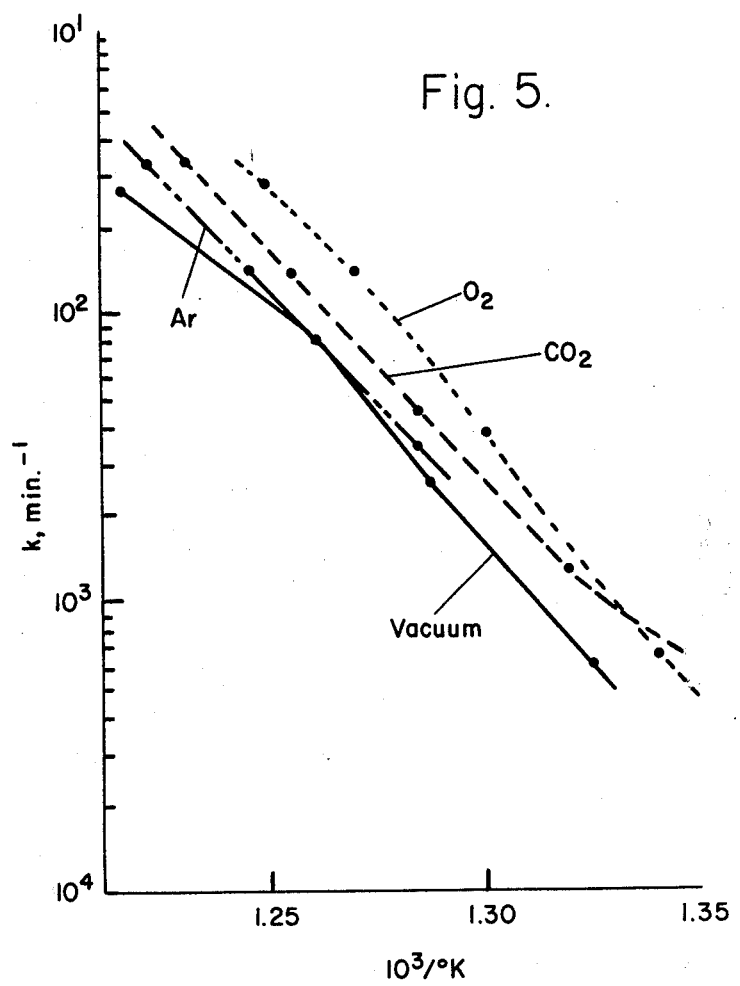
FIG. 5 is a graph which shows the decay constant (k) as a function of the depolymerization temperature of Teflon under various atmospheres.

The temperature required to depolymerize Teflon, and thus the forward rate of Eq. (3), is strongly dependent upon the decomposition environment. FIG. 5 graphically shows this dependence. At each temperature setting from 470° to 545° C., independent of the atmosphere provided, the weight loss per unit time was proportional to the weight of the residue.

These results enabled us to choose a depolymerization temperature, weight of residue, and flow rate of carrier gas to determine the partial pressure of C$_2$F$_4$ in the mixture, which enters the second stage ampoule 16 of the apparatus shown in FIG. 4, and the practical temperature and length of time to operate the generator.

The second stage of the apparatus may be characterized as an elongated ampoule having a restricted tubular entrance 17, which leads from the first stage ampoule 13 and functions as the exit passage for depolymerized Teflon (mainly C$_2$F$_4$) and carrier gas, a constant diameter tubular section 18, and a restricted tubular exit 19 on the opposite end. Disposed intermediate the restricted tubular portions of this ampoule about the constant diameter section periphery is a second furnace 20 used to elevate the interior of the ampoule to the dissociation temperature of C$_2$F$_4$.

C$_2$F$_4$ gas mixed with an inert carrier gas entering the second stage ampoule 16 is further heated to their dissociation temperature, by the action of the second furnace 20, to produce C and $CF_4$.

Carbon particles 22, produced by the dissociation of $C_2F_4$, condense and are trapped along the relatively cooler converging portion 21 of the ampoule lying between the constant diameter section 18 and the restricted tubular exit section 19, while $CF_4$ gas is carried from the chamber in the carrier gas.

The exit section 19 of the $CF_4$ reactor or generator may be connected to a gas chromatograph for the purpose of monitoring the amount and quality of the $CF_4$ effluent to be fed into a crystal growth apparatus.

In order to optimize the depolymerization of Teflon, in accordance with Equation (3), a series of tests were conducted in which the weight loss of Teflon as a function of time and temperature was monitored via thermal gravimetric analysis (TGA). Specific quantities of Teflon were subjected to various atmospheric purges at a series of elevated temperatures. Data acquired from these tests, when utilized in connection with the following equation, enabled us to establish the decay constant, k vs. temperature profile shown in FIG. 5.

$$\frac{W}{W_0} = e^{-kt} \quad (5)$$

where W is the weight of Teflon, at any time, $W_0$ is the initial weight of Teflon, and t is the time of exposure of Teflon to the elevated temperature which determines the value of k.

From the results of these tests, as presented in FIG. 5, one is then able to select a Teflon depolymerization temperature and accurately predict the amount of $C_2F_4$ that is generated at that temperature in the presence of the particular carrier gas since the amount of $C_2F_4$ is essentially equal to $W_0 - W$.

$C_2F_4$ generated via the depolymerization of Teflon is then carried from the first stage 13 of the apparatus into the second stage 16 of the apparatus by a chosen carrier gas at a flow rate designed to ensure a $C_2F_4$-Carrier gas mixture dwell time within the second stage from 5 to 10 minutes. The second stage has been previously raised to a temperature sufficient to cause near complete dissociation of $C_2F_4$ to C and $CF_4$.

We have discovered that $C_2F_4$ will dissociate into $CF_4$ and C in accordance with Equation 4 at temperatures as low as 800° C. When He is employed as the carrier gas and a flow rate of approximately 50 $cm^3$/min is maintained, essentially all of the $C_2F_4$ is converted into $CF_4$ and C below 900° C. within 10 minutes using a pyrolysis chamber having a volume of approximately 500 cc.

Figure 6:
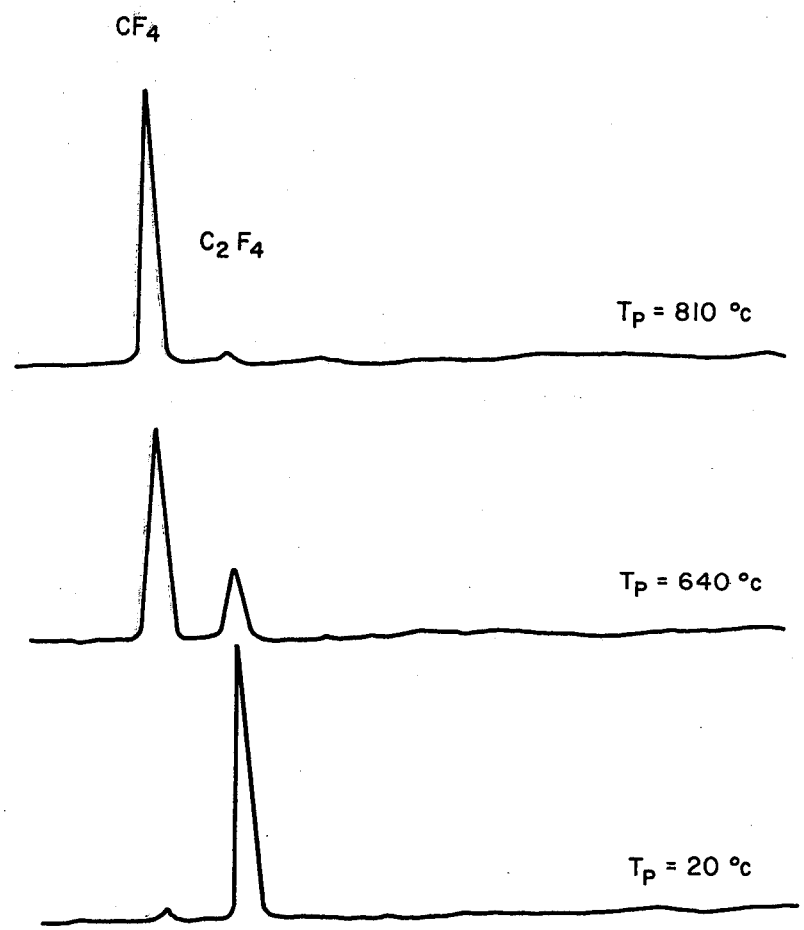
FIG. 6 presents the results of gas chromatographic analyses of the generator effluent gases which shows that the product becomes increasingly richer in CF$_4$ as the temperature is increased from 20° to 810° C.

The presence of $CF_4$ as the major component of the apparatus effluent gas at various pyrolysis temperatures was ascertained via chromatographic analyses of this gas. FIG. 6 shows the effect of the pyrolysis temperature (Tp) on the composition of the effluent gas when He is used as a carrier and Teflon was subjected to a depolymerization temperature of 425° C. $C_2F_4$ gas emanating from the depolymerization of Teflon was subjected to a residence time within the quartz pyrolysis chamber of 30 minutes at each of the temperatures shown in FIG. 6.

An example of the use of the process to generate $CF_4$ for the growth of $CaF_2$ crystals from 1.84g of $CaCO_3$ as a starting material is shown where 88.3g of Teflon 14 is placed in the reactor section 13 of the apparatus shown in FIG. 4. A He gas purge of $\cong$ 60 $cm^3$/min is provided by causing He to enter the reactor through the gas inlet means 12. The temperature of the reactor is raised to approximately 480° C. which causes the Teflon to depolymerize into $C_2F_4$ thereby creating a $C_2F_4$-He gas mixture.

The $C_2F_4$-He gas mixture is then allowed to enter the pyrolysis chamber 16 or second stage of the apparatus which has been heated to 900° C. Here $CF_4$ and elemental carbon is formed from the dissociation of $C_2F_4$. The dwell or residence time of the $C_2F_4$-He mixture in the pyrolysis chamber was approximately 10 minutes.

Effluent gas comprised of $CF_4$ from the apparatus then passes into an astro furnace charged with 1.84g of $CaCO_3$. The Astro furnace temperature is slowly raised from ambient temperature to 1200° C. The $CF_4$ is allowed to impinge on CaO, formed by the dissociation of $CaCO_3$, for approximately 8 hours. At this point in time, all of the $CaCO_3$ will have been converted into $CaF_2$. The $CaF_2$ is then melted by raising the furnace temperature to 1500° C. in the presence of a continuous flow of $CF_4$ from the reactor and maintained for 60 minutes.

A subsequent examination of the reaction product showed that a 100% conversion of $CaCO_3$ to $CaF_2$ had been effected. During the course of the experiment, actually 23.3g of Teflon was consumed which produced 0.233 moles of $C_2F_4$ which yielded 0.233 moles of $CF_4$ in the presence of 0.0184 moles of $CaCO_3$ to yield precisely 0.0184 moles of $CaF_2$.

Elemental carbon condensed and collected on the relative cooler converging section of the apparatus.

From our $CF_4$ generation studies, we have concluded that the preferred carrier gas is helium although other inert gases may be used. A depolymerization temperature of 482° C. appears to produce $C_2F_4$ from Teflon at a rate suitable for large scale alkaline earth flouride crystal growth.

A flow rate of 60 $cm^3$/min facilitates the exposure of $C_2F_4$ gas to its pyrolysis temperature for from 5 to 10 minutes which proves more than adequate to cause it to dissociate into $CF_4$ and C when the pyrolysis chamber is heated to at least 800° C. A temperature of 810° C. has been utilized with great success, and temperatures less than 910° C. will prove to be adequate for almost all applications.

Having fully disclosed our invention and presented ways to make and use it, the scope of our claims to this invention may now be understood as follows.

What is claimed is:

1. A controllable process for generating $CF_4$ from commercially available polytetrafluoroethylene comprising the steps of:
   (a) charging a depolymerization reactor with precisely known quantities of tetrafluoroethylene;
   (b) selecting a reactor temperature, from a plot of tetrafluoroethylene decay constants versus temperature, which provides for the generation of $C_2F_4$ at a desired rate;
   (c) creating an atmospheric purge by causing an inert carrier gas to flow through said reactor;
   (d) raising the temperature of said reactor to said selected temperature thereby causing a $C_2F_4$-purge gas mixture to be formed within said reactor;
   (e) directing said $C_2F_4$-purge gas mixture from said reactor into a pyrolysis chamber, previously heated to a temperature high enough to cause the $C_2F_4$ component of said mixture to decompose into known amounts of $CF_4$ and elemental carbon, at a flow rate sufficient to insure a gas mixture dwell time within said chamber of from 5 to 15 minutes; and (f) removing said $CF_4$ from said chamber with said carrier gas while allowing said elemental carbon to be trapped along the relatively cool walls of said chamber.

2. The process of claim 1 wherein said carrier gas is selected from the group consisting of Helium, Argon, Nitrogen and carbon dioxide, said reactor temperature ranges from 425° to 525° C. and said pyrolysis chamber temperature ranges from 800° to about 900° C.

3. The process of claim 1 wherein said carrier gas is He, said reactor temperature is 482° C. and said pyrolysis chamber temperature is set to approximately 810° C.

4. A process for generating $CF_4$ which comprises:
(a) depolymerizing polytetrafluoroethylene in the presence of a carrier gas purge at an elevated temperature to form a mixture of $C_2F_4$ and said carrier gas;
(b) heating said mixture to an elevated temperature and maintaining said mixture at said temperature for a time sufficient to cause said mixture to dissociate into a mixture of inert gas, $CF_4$ and carbon; and
(c) selectively removing said carbon from said mixture of $CF_4$ and carbon.

5. The process of claim 4 wherein said carrier gas is selected from the group consisting of He, Ar, $N_2$, and $CO_2$, said depolymerization temperature is on the order of 450° C. and said $C_2F_4$ mixture is heated at an elevated temperature on the order of 850° C. for a time period ranging from 5 to 15 minutes.

6. The process of claim 5 wherein said carrier gas is He.

* * * * *